United States Patent [19]

Hara et al.

[11] Patent Number: 4,508,453
[45] Date of Patent: Apr. 2, 1985

[54] PATTERN DETECTION SYSTEM

[75] Inventors: Yasuhiko Hara; Nobuyuki Akiyama; Satoru Fushimi; Yoshimasa Oshima; Nobuhiko Aoki, all of Yokohama, Japan

[73] Assignee: Hitachi, Ltd., Tokyo, Japan

[21] Appl. No.: 397,900

[22] Filed: Jul. 13, 1982

[30] Foreign Application Priority Data

Jul. 14, 1981 [JP] Japan .................. 56-108885
Oct. 19, 1981 [JP] Japan .................. 56-165744
Nov. 6, 1981 [JP] Japan .................. 56-177161

[51] Int. Cl.$^3$ ............................................. H06N 7/18
[52] U.S. Cl. ............................ 356/394; 358/106
[58] Field of Search ............... 356/390, 394, 398; 358/106, 206, 293

[56] References Cited

U.S. PATENT DOCUMENTS

| | | | |
|---|---|---|---|
| 4,112,469 | 9/1978 | Paranjpe et al. | 358/293 |
| 4,148,065 | 4/1979 | Nakagawa et al. | 358/106 |
| 4,185,298 | 1/1980 | Billet et al. | 356/390 |
| 4,209,257 | 6/1980 | Uchiyama et al. | 356/394 |
| 4,274,745 | 6/1981 | Takahashi et al. | 356/427 |
| 4,277,175 | 7/1981 | Karasaki et al. | 356/394 |
| 4,389,669 | 6/1983 | Epstein et al. | 358/106 |

FOREIGN PATENT DOCUMENTS 87748 7/1956 Norway .................. 356/394

OTHER PUBLICATIONS

Simms, "The Application of CCD's to Document Scanning", Microelectronics, vol. 7, No. 2 (Dec. 1975), pp. 60-63.

Primary Examiner—R. A. Rosenberger
Attorney, Agent, or Firm—Antonelli, Terry & Wands

[57] ABSTRACT

A pattern detection system for inspecting defects in fine or minute patterns such as photomask patterns at a fast speed is disclosed. The system comprises an illuminator, a device for moving objects with the patterns to be inspected with being illuminated by the illuminator, an optical system for imaging the objects, a scanner for scanning the objects in a direction intersected at a given angle with respect to direction of the objects moved by the moving device and arrays of photosensors arranged linearly in a direction perpendicular to that of images on the objects scanned by the scanner, on the surface of which the images are formed by the optical system and for producing respective outputs parallelly on the time basis.

11 Claims, 39 Drawing Figures

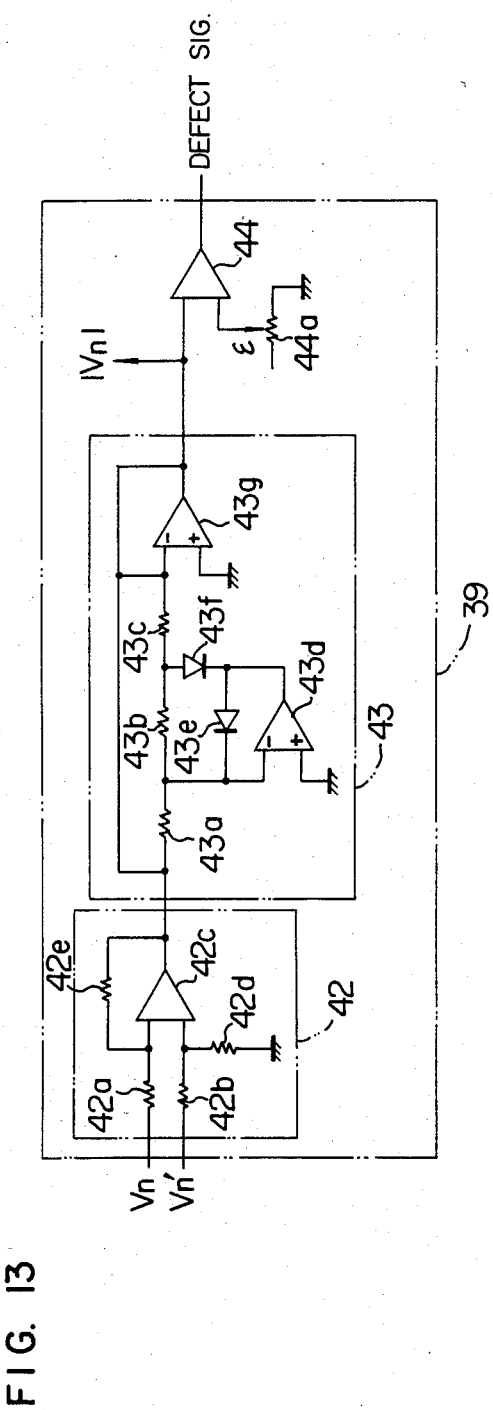
F I G. 13
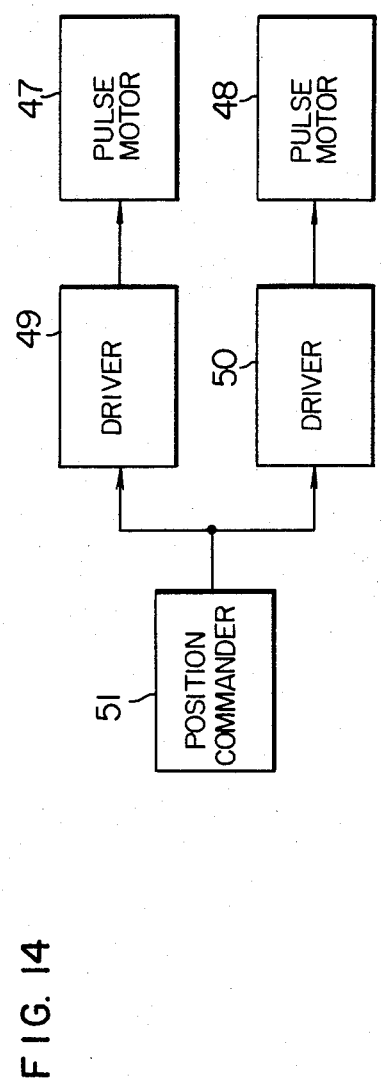
F I G. 14

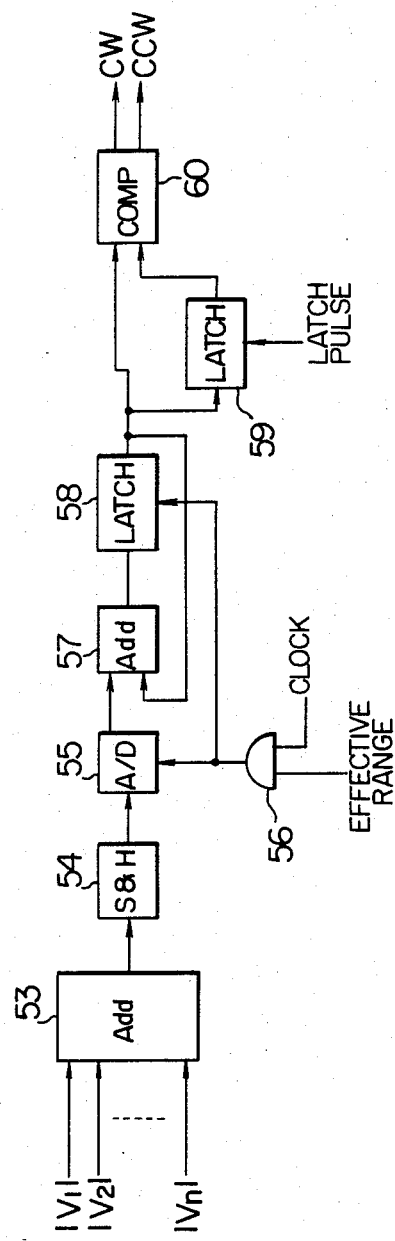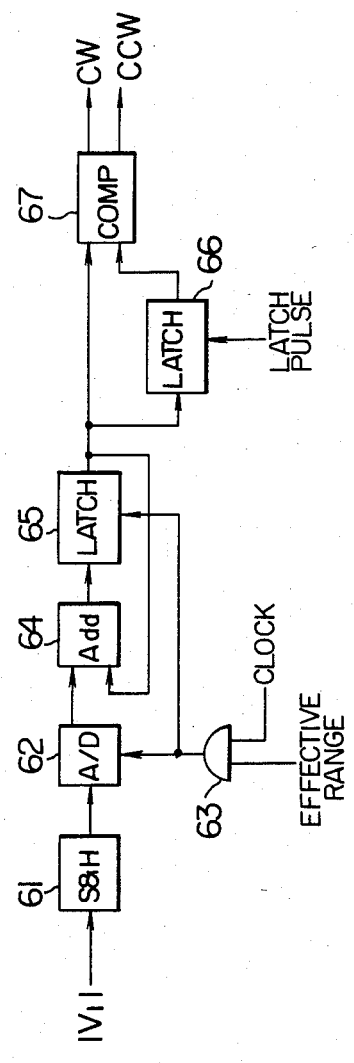
F I G. 16
F I G. 17

PATTERN DETECTION SYSTEM

The present invention relates to a pattern detection system, more particularly to a system for detecting, at a high speed, defects in fine or minute patterns such as photomask patterns used in production of semiconductor integrated circuits or aluminum (Al) circuit patterns formed on semiconductor wafers.

There has been, so far, suggested a method of detecting pattern defects wherein, for example, in fabricating a lot of integrated circuits at the same time with use of a photomask formed with a lot of equally-spaced circuit patterns of the same configuration, any two of the circuit patterns are detected and compared to thereby determine if the two are completely matched in configuration, that both are normal, while if not, there exist defects in the two circuit patterns.

The principles of different prior-art pattern detection systems based on the method of the type referred to above are shown in FIG. 1 and FIG. 2.

In the system shown in FIG. 1, a photomask is placed on a table 1 which is movable in X and Y directions. Lights are directed from a light source 3 (arranged on the bottom side of the photomask 2) through reflection mirrors 4 and 4' and condensers 5 and 5' onto two pattern zones of the photomask 2 under inspection. The lights transmitted through the table 1 and the mask 2 are magnified through microscope lenses and 6 and 6' and imaged on array sensors 7 and 7' each of which comprise a multiplicity of photosensors linearly arranged. The light and darkness level of the images formed on the array sensors are converted to electric signals and applied to respective binary conversion circuits 8 and 8' where they are converted to binary picture element (pixel) signals. The binary picture signals are stored in respective video memories 9 and 9'. As the table 1 is moved in a direction perpendicular to the linear array sensors 7 and 7', the video memories 9 and 9' sequentially read the respective binary picture element signals for comparison check by a comparator 10.

In the system shown in FIG. 2, on the other hand, bright spots from a flying-spot tube or scanner 11 are linearly scanned on the mask 2 under control of a control circuit 15, so that the bright spots are imaged on any two pattern zones of the photomask through respective imaging lenses 12 and 12', and the lights which pass through the mask and the table from the imaging lenses are focused on respective photo-sensors 14 and 14' via condensers 13 and 13' to convert them to electric signals whose magnitude varies according to the amount of transmitted light due to the absence or presence of patterns on the mask. As the table 1 is moved in a direction perpendicular to the scanning direction of the flying-spot tube, the two electric signals from the photo-sensors 14 and 14' are compared by a comparator 16 for pattern check.

In pattern detection by the prior art pattern detection system, detection signals are obtained by scanning the linear array sensors or flying-spot tube on a pattern surface $2a$ sequentially in arrow directions of $A_1$, $A_2$, $A_3$, ..., as shown in FIG. 3. The detection signals are time-series voltage signals which vary according to the light and darkness level on the pattern surface, and when scanning is made in the arrow $A_1$ direction in FIG. 3 such a detection signal $7a$ as shown in FIG. 4 is obtained. A length l on the pattern surface $2a$ in FIG. 3 corresponds to a time "t" in FIG. 4.

In a similar way, a detection signal $7a'$ is detected by arrow $A_2$ scanning, and a detection signal $7a''$ is detected by arrow $A_3$ scanning, the detection signal $7a'$ followed by the detection signal $7a''$ on a time basis.

In such a pattern detection method, the scanning speed must be increased in order to increase the detection speed. However, when the scanning speed increases, the detection signals $7a$ and $7a'$ will vary faster with time, which shortens the time necessary to store the light energy and convert it to electric signals, so that the sensitivity of the sensor is deteriorated. In addition, since the detection signals $7a$ and $7a'$ change fast, there is difficulty in handling the signals. For these reasons, such a detection method of scanning the pattern surface $2a$ sequentially in the order of $A_1$, $A_2$, $A_3$ ... is restricted when a higher detection speed is required.

Accordingly, it is an object of the present invention to provide a novel pattern detection system which realizes a substantial reduction of the necessary detection time.

According to one of the features of the invention, there is provided a pattern detection system wherein, in order to detect mask patterns to be inspected which are placed on a movable table, light paths in an optical imaging system are repeatedly offset or displaced at a high speed, for example, by a rotary multi-face mirror to thereby scan the mask pattern images on the imaging surfaces at a high speed in a direction substantially perpendicular to the table movement direction, i.e., mask movement direction, and wherein a multiplicity of photo-sensors for each mask pattern are arranged in the imaging surface of at least one row perpendicular to the image scanning direction to detect in parallel, signals from the respective photo-sensors in synchronism with the image scanning operation, whereby a pattern included in a rectangular plane defined by an image scanning distance and the length of the at least one row of photo-sensors can be detected in one scanning time and the inspection speed can be improved by the amount of inspection speed in a prior-art system multiplied by the number of photo-sensors in the one row.

The above pattern detection system according to the invention is further characterized in that light receiving portions of N photo-sensors are arranged in a straight line L so that output signals from the photo-sensors are generated simultaneously and parallelly, and the mask pattern images are scanned in a direction perpendicular to said straight line L while the patterns are moved or fed in a direction parallel to the line L at a speed $V=W/T$, where W is the scan width of one of the light receiving portions of N photo-sensors arranged in the line L, T is the scan cycle time and N is a positive integer equal to or greater than 2.

According to a further feature of the present invention, the light receiving portions of the photo-sensors are each shaped into a rectangle or square, two rows of photo-sensors (N photo-sensors in one line) are arranged in a parallel positional relation to each other and the light receiving portions in one row are disposed as offset by half of a pitch of the light receiving portion with respect to the light receiving portions in another row, so that, at the time of parallel outputting, i.e., at the time picture element output signals are separately issued from the adjacent light receiving portions, either one of the two rows positively locates or finds pattern defects to prevent quantizing errors.

According to another feature of the invention, in order to automatically detect pattern defects, adhered foreign matter or abnormal compositions on a plurality of test or specimen chips having fine or minute patterns, such as LSI wafers, a detecting zone on the chips is magnified with a microscope, two video detection elements are provided in a real image surface for a quantitative analysis of the relationship between the detected video signals to thereby obtain an actual positional offset signal $D_x$ without being affected by the configuration and number of the detecting patterns. Further, means is provided for detecting the pattern direction in the video, so that when an X direction pattern appears the pattern direction detecting means determines the actual positional offset amount in the Y-direction and generates a $D_x$ signal, and when a Y-direction pattern appears the pattern direction detecting means determines the actual positional offset amount in the X-direction and generates the $D_x$ signal, whereby fine and coarse displacement mechanisms are actuated by the $D_x$ signals to displace two light fibers relatively and align precisely and quickly the corresponding detecting points on the two chips with each other.

A still further feature of the invention is that two points on the wafer are intensely dark-field illuminated with use of a parabolic concave mirror and the dark field illumination is combined with light field illumination to thereby inspect automatically the configurations of patterns on an LSI wafer and the like.

The present invention will be apparent from the following detailed description taken in conjunction with the accompany drawings, in which:

FIG. 1 schematically shows an arrangement of an exemplary prior-art pattern detection system;

FIG. 2 schematically shows an arrangement of another exemplary prior-art pattern detection system;

Figure 1:
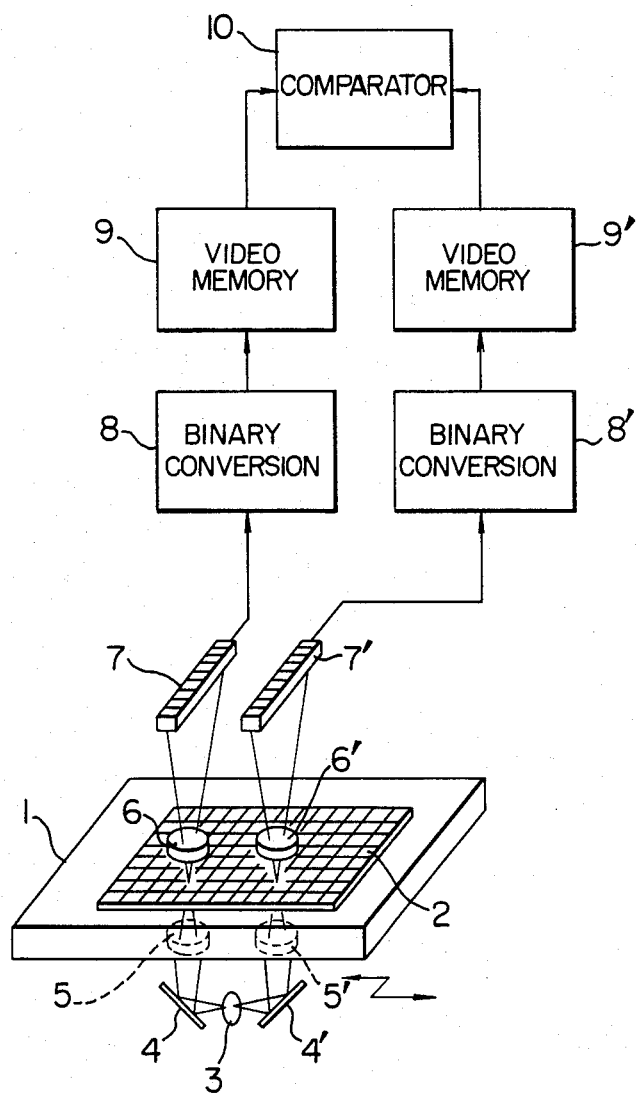
Figure 2:
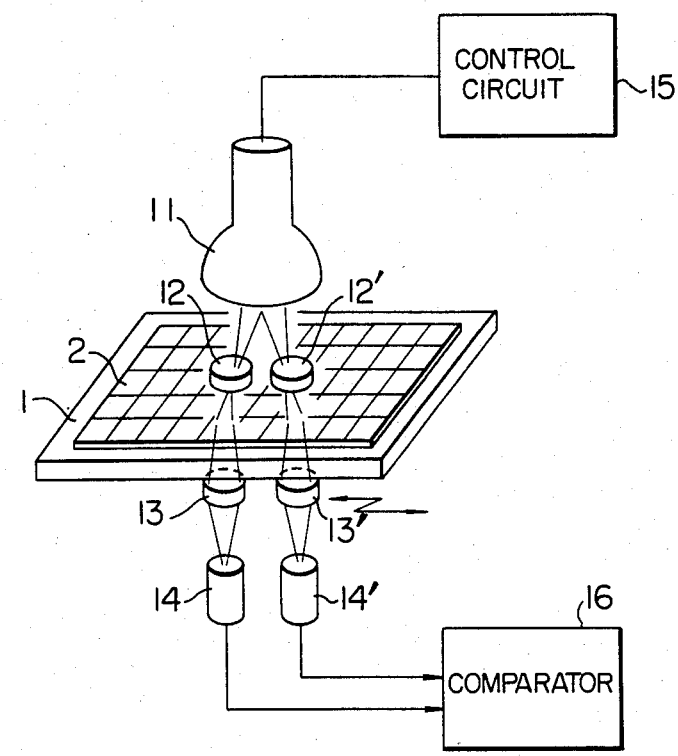
Figure 3:
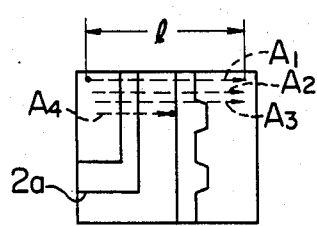
FIG. 3 shows a top view of a pattern surface for explanation of a widely-used pattern detection method.
Figure 4:
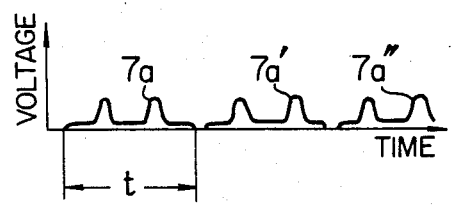
FIG. 4 shows waveforms of signals detected by the method of FIG. 3.
Figure 5:
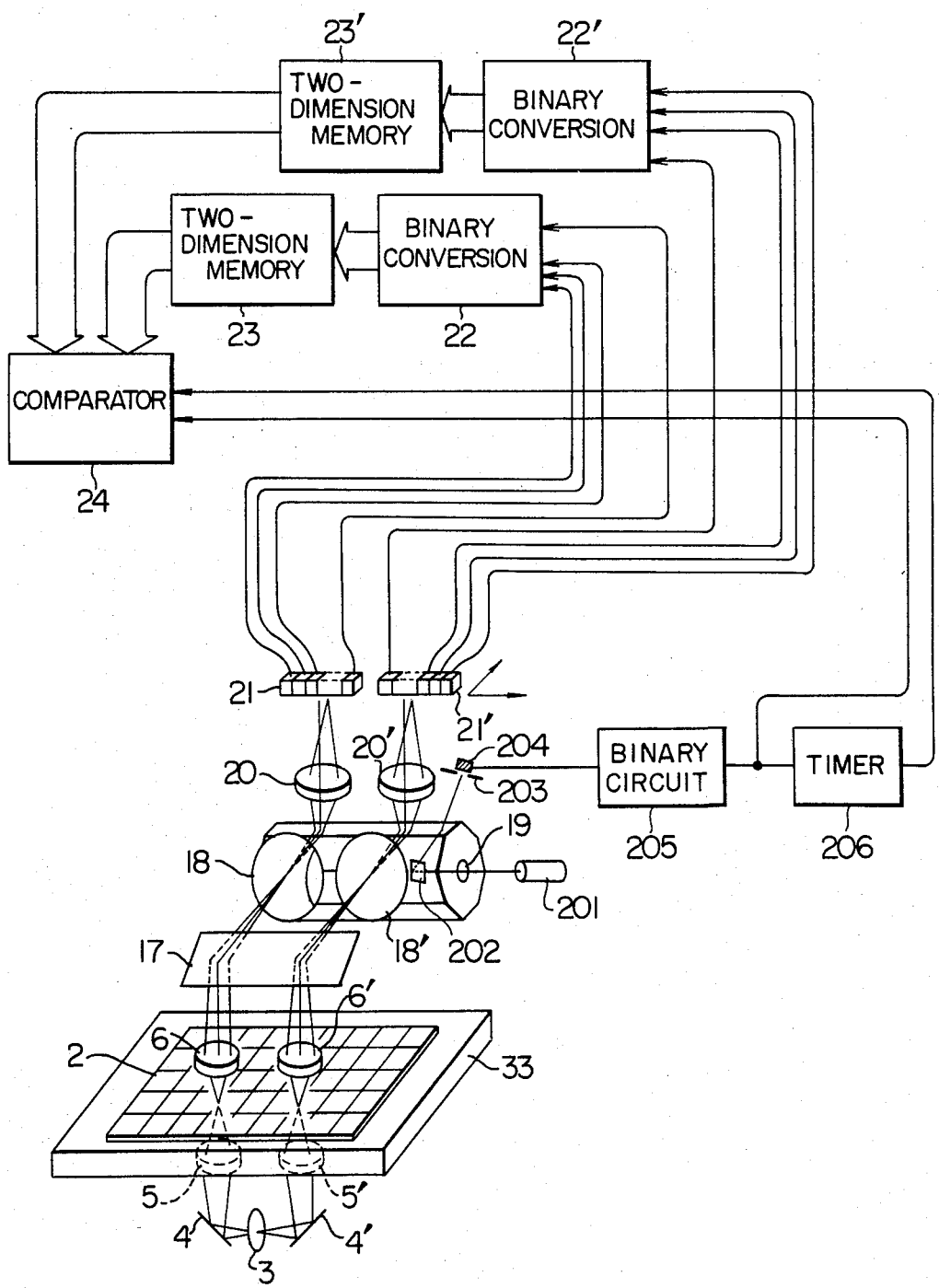
Figure 6:
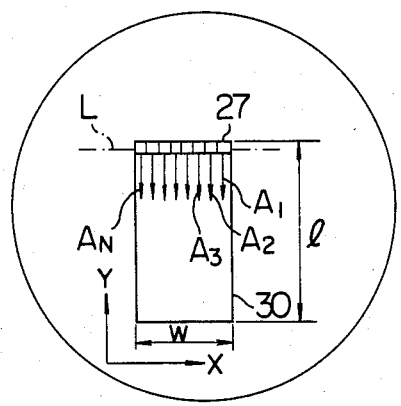
Figure 7:
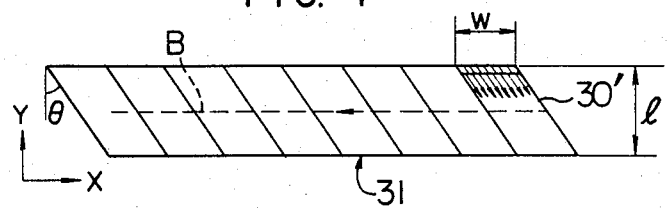
Figure 8:
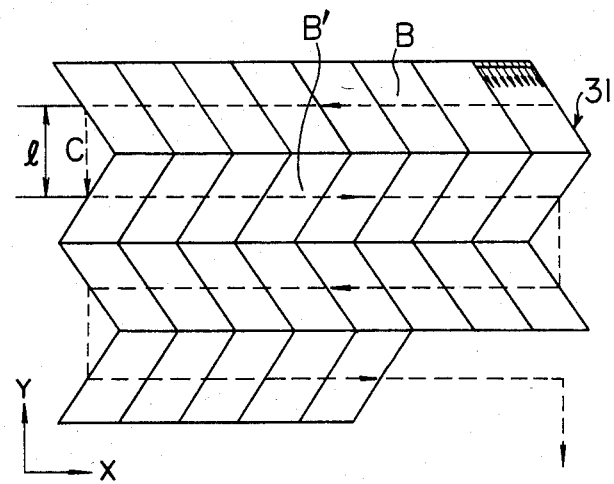
Figure 9:
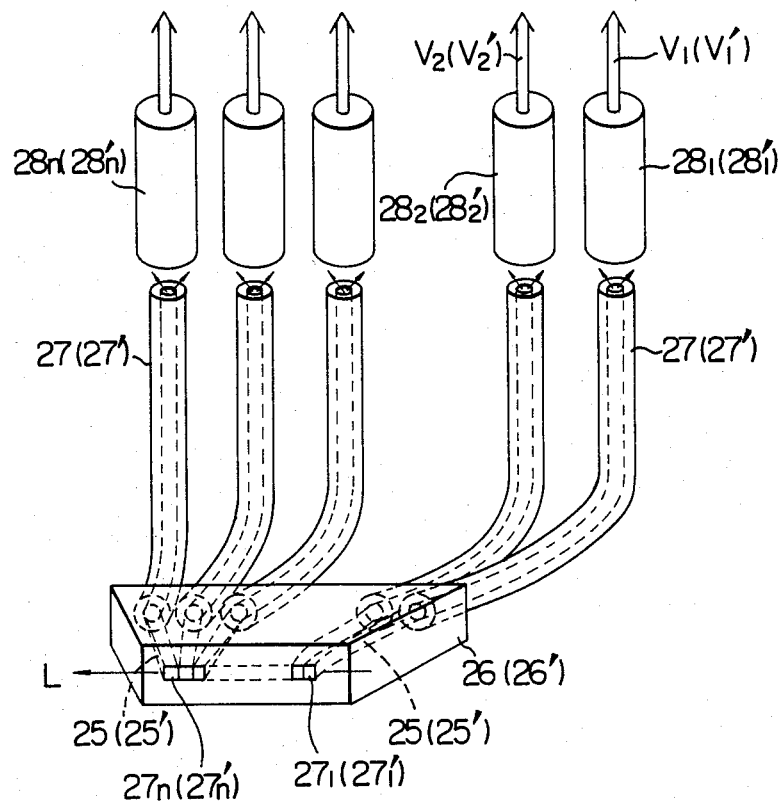
Figure 10:
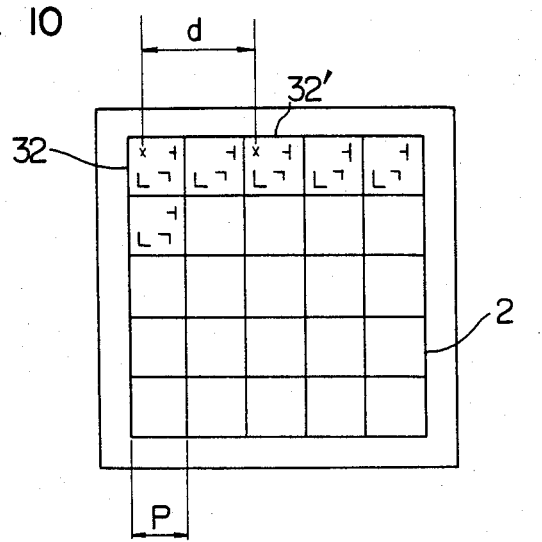
Figure 11:
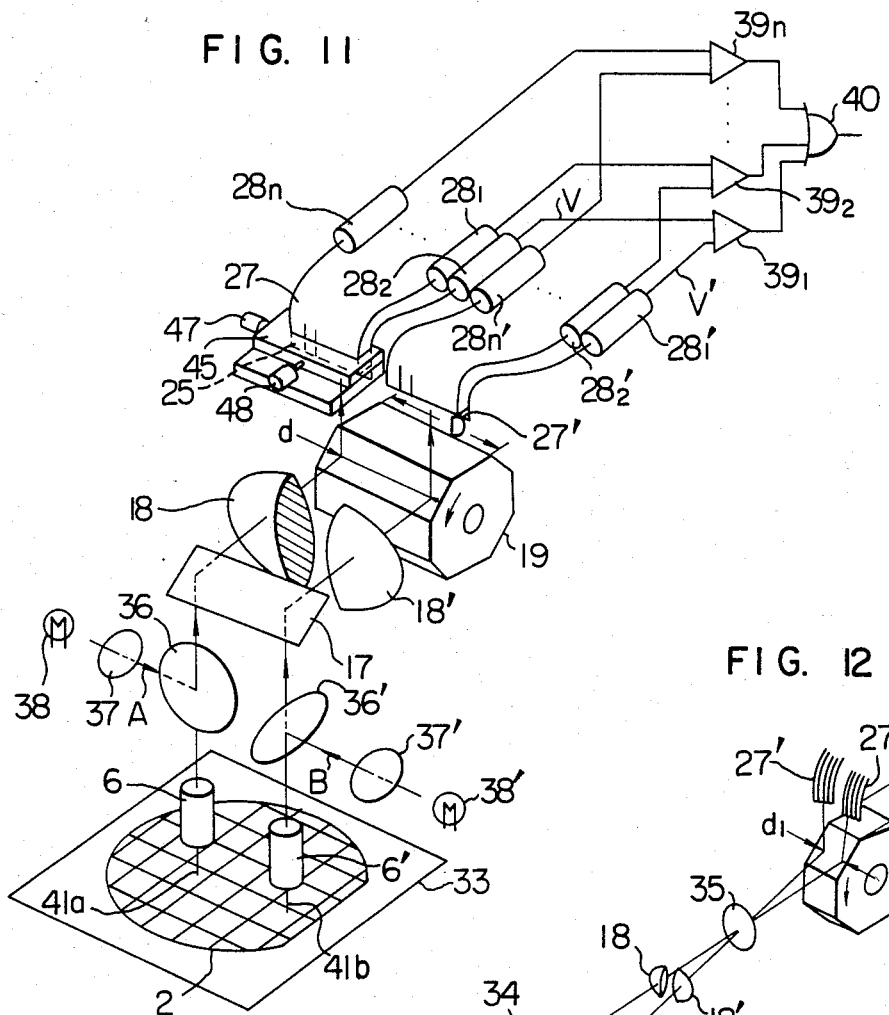
Figure 12:
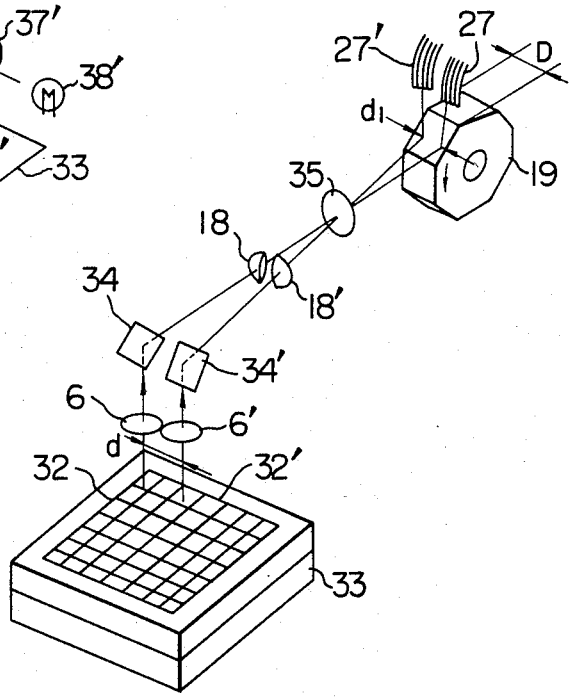
Figure 15:
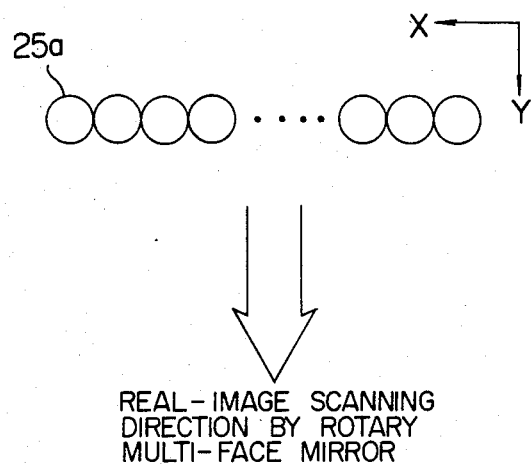
Figure 18:
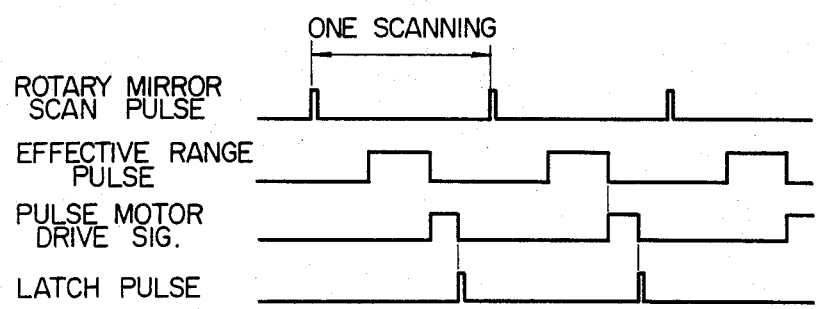
Figure 19:
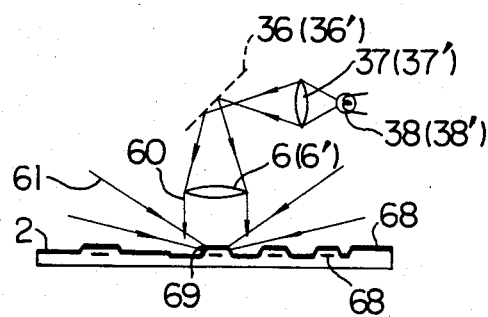
Figure 20:
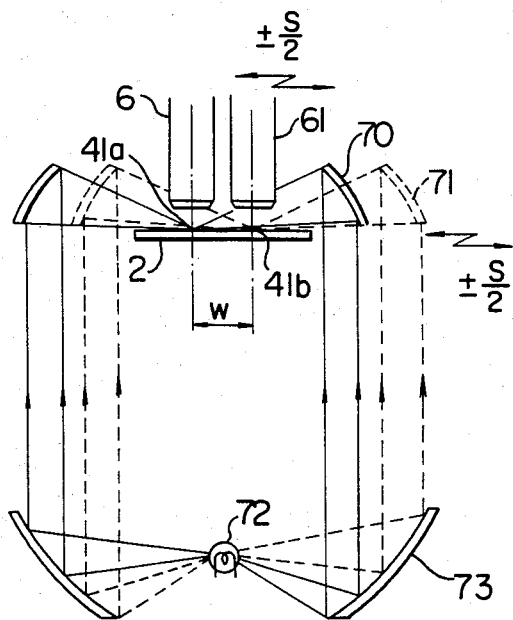
Figure 21A:
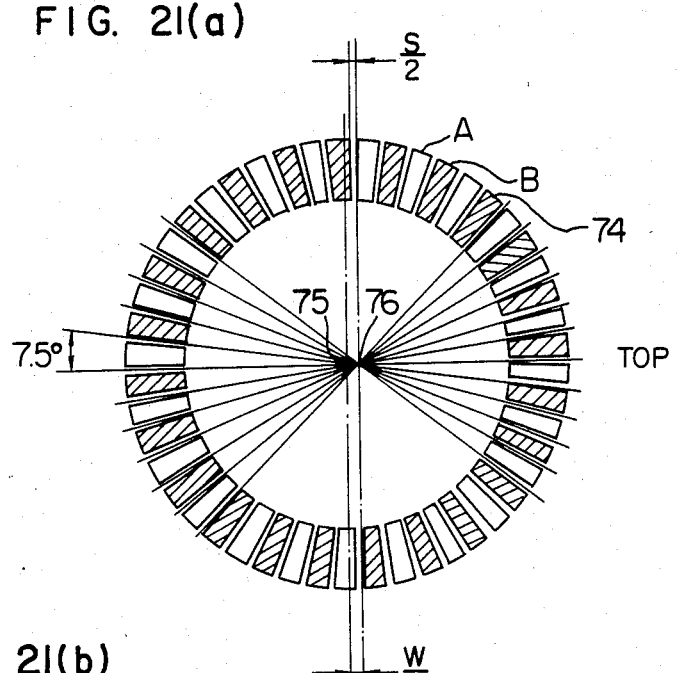
Figure 21B:
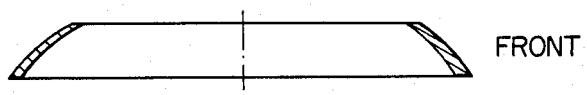
Figure 22:
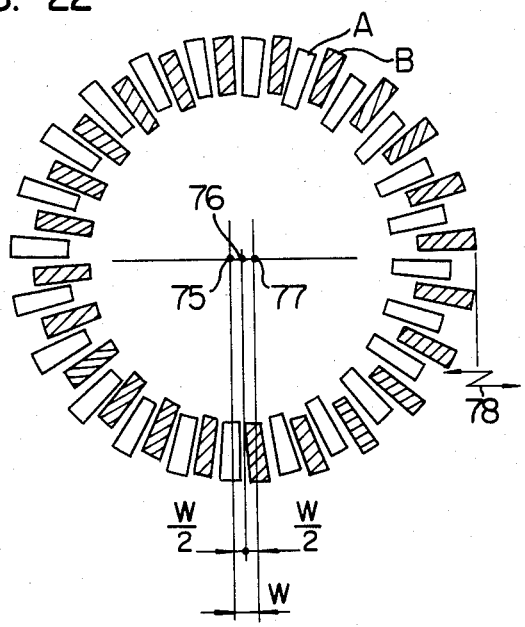
Figure 23A:
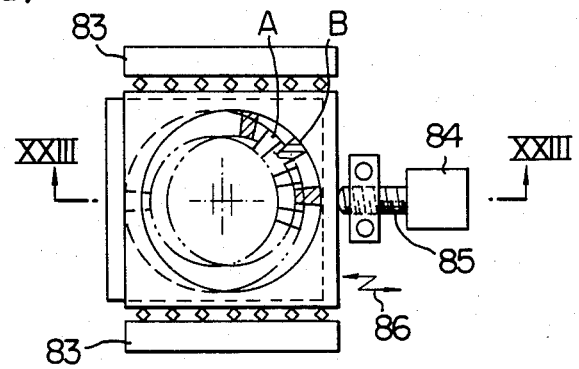
Figure 23B:
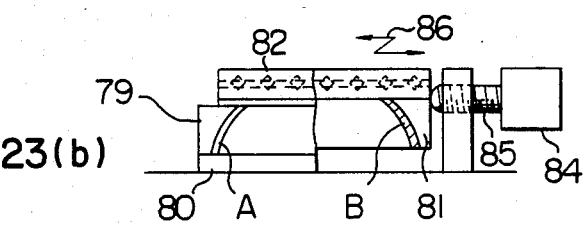
Figure 24A:
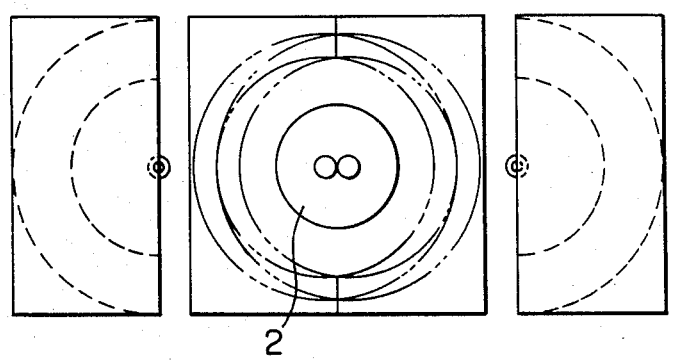
Figure 24B:
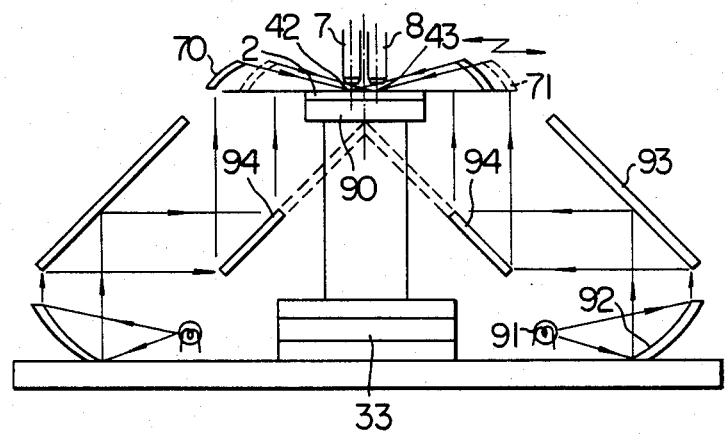
Figure 25:
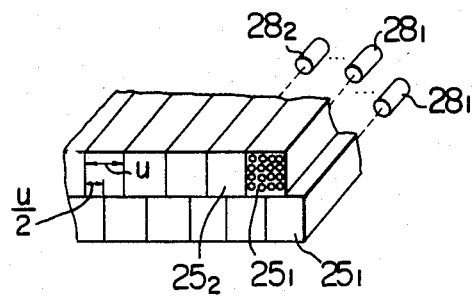
Figure 26:
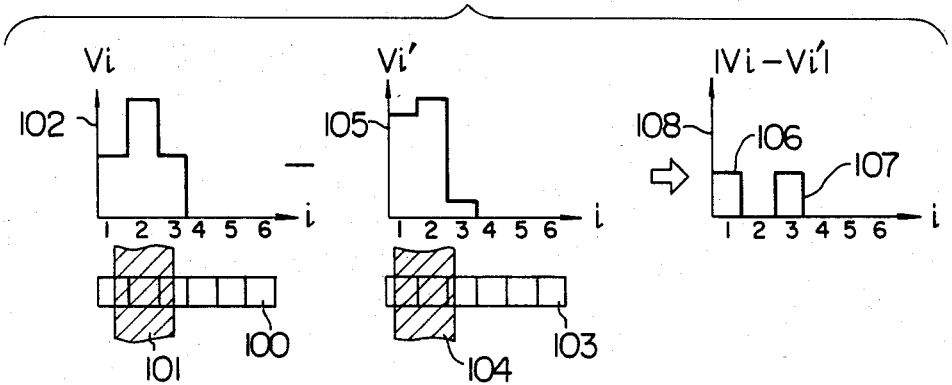
Figure 27:
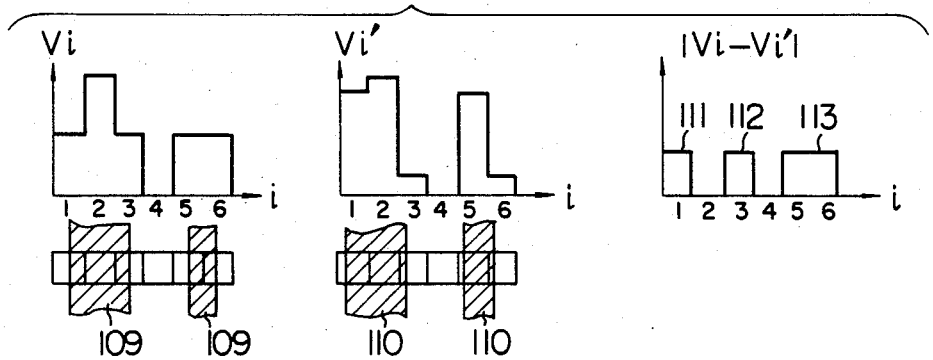
Figure 28:
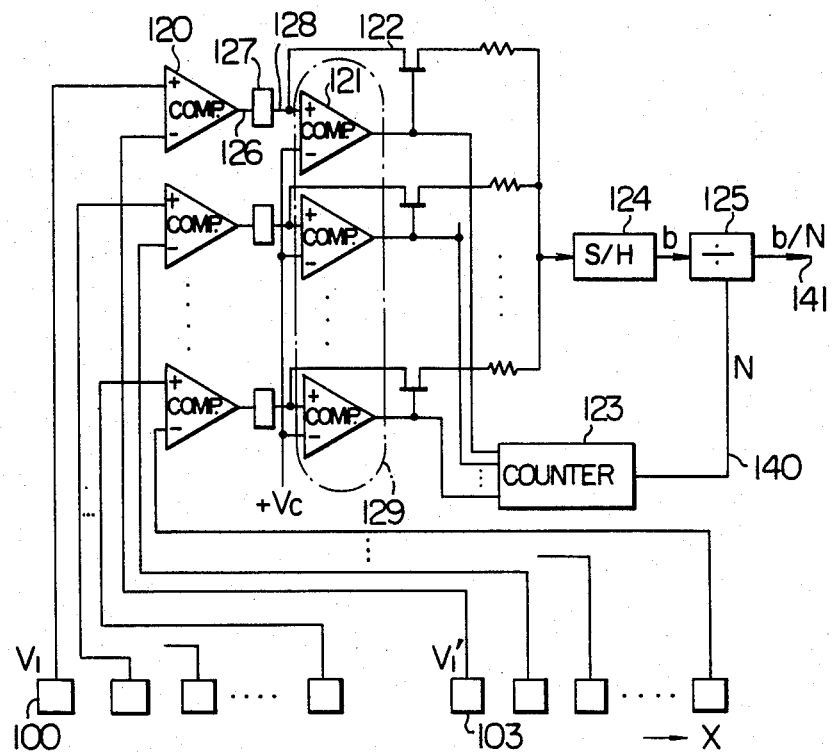
Figure 30:
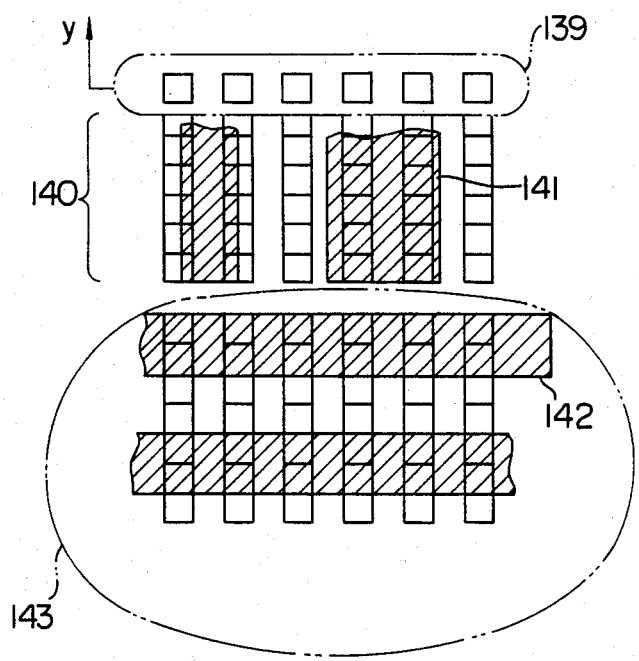
Figure 29:
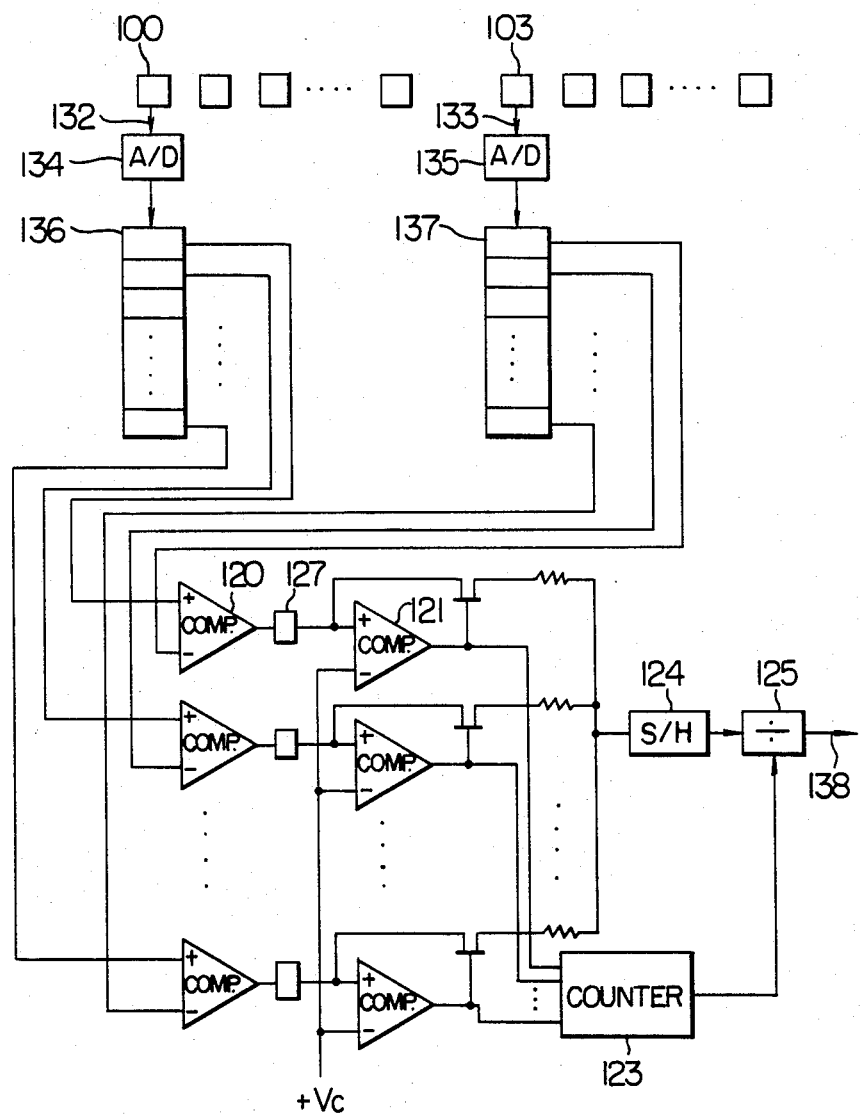
Figure 31:
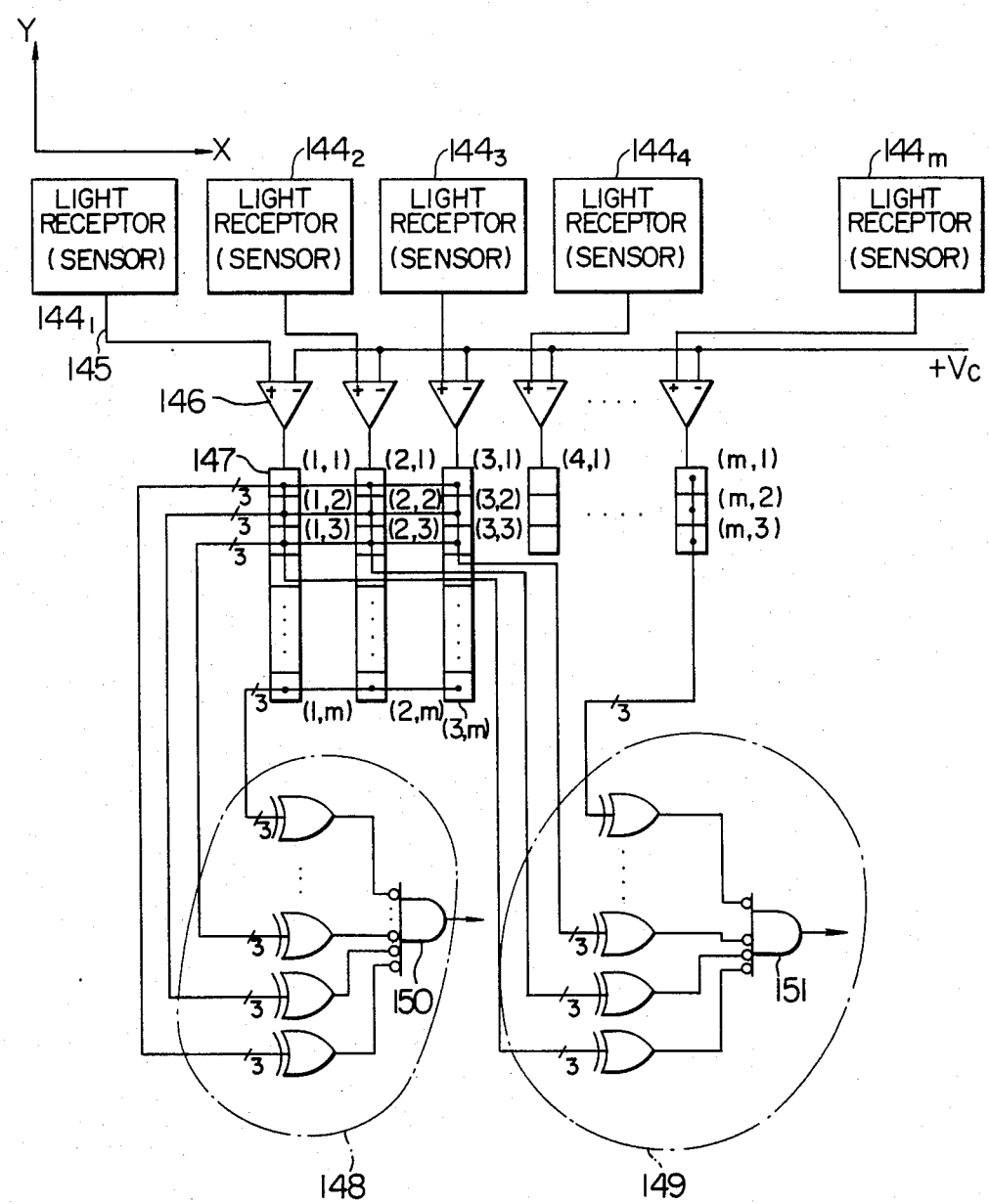
Figure 32A:
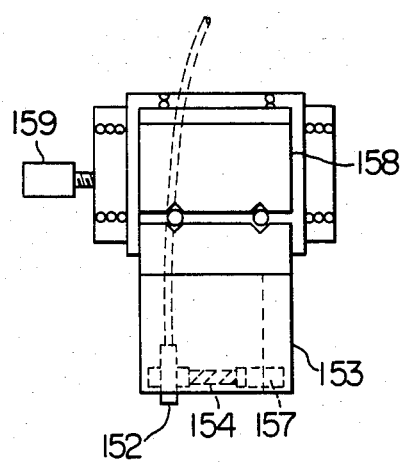
Figure 32B:
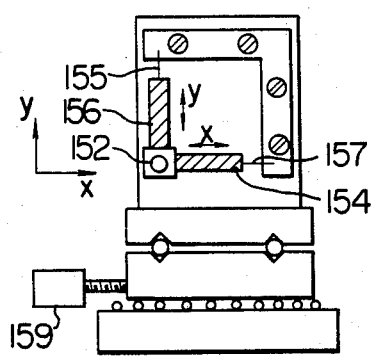
Figure 32C:
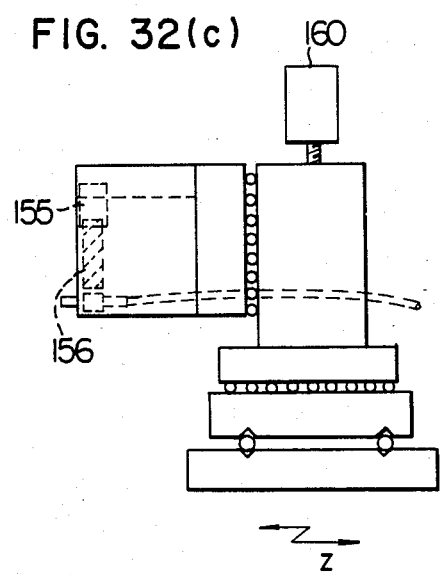
Figure 33:
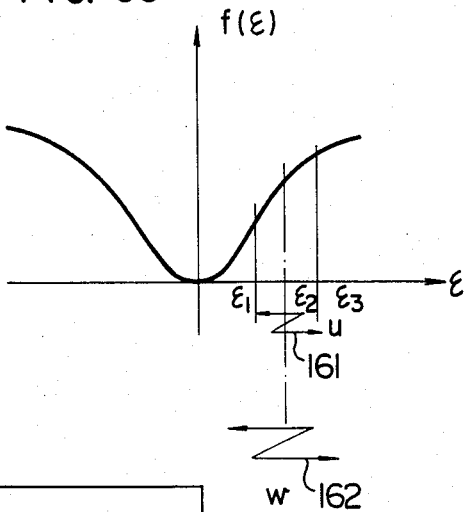
Figure 34:
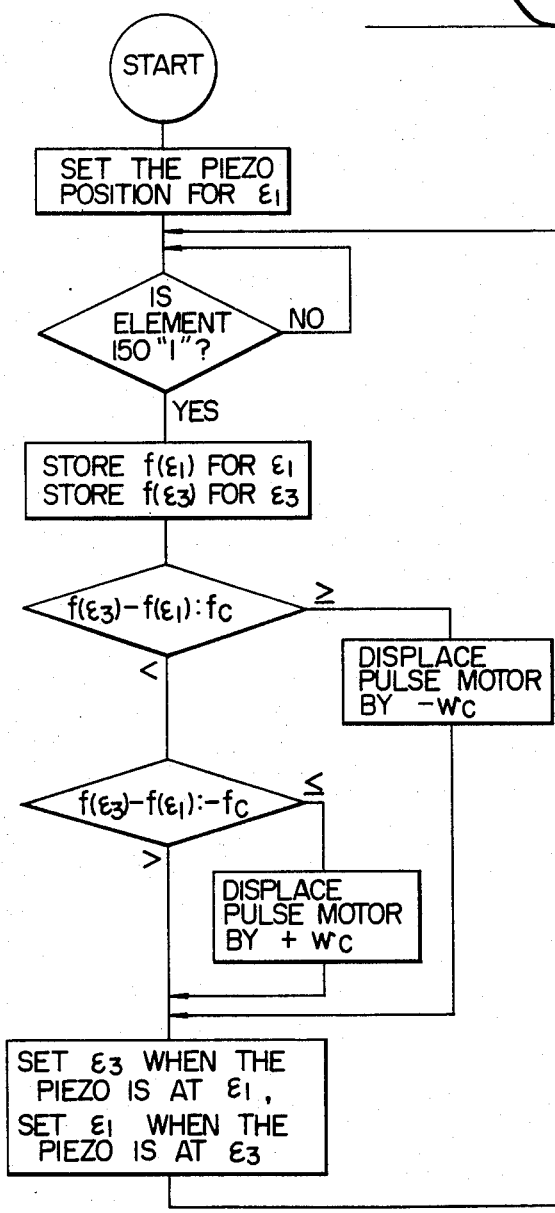

FIG. 5 diagrammatically shows an embodiment of a pattern detection system in accordance with the present invention;

FIG. 6 is a plan view of the field of view in an optical system shown in FIG. 5;

FIGS. 7 and 8 show top views of exemplary scanning zones by the system of FIG. 5;

FIG. 9 diagrammatically shows another form of detectors used in the embodiment;

FIG. 10 shows an exemplanary photomask to be inspected available in the system of the invention;

FIG. 11 diagrammatically shows another embodiment of the pattern detection system in accordance with the present invention;

FIG. 12 diagrammatically shows a further embodiment of the pattern detection system in accordance with the present invention;

FIG. 13 shows a circuit diagarm of a form of comparator used in the system of the invention;

FIG. 14 shows a block diagram of a driver for driving a table, used in the system of the invention;

FIG. 15 is an explanatory view showing a relationship between the light receiving surfaces of optical fibers and the scanning direction;

FIG. 16 shows a block diagram of a form of X-direction positional offset calculator circuit used in the system of the invention;

FIG. 17 shows a block diagram of a form of X-direction positional offset calculator circuit used in the system of the invention;

FIG. 18 shows a timing chart of signals appearing in the offset calculator circuits of FIGS. 16 and 17;

FIG. 19 is an explanatory view showing a light field illumination system in the pattern detection system of the invention;

FIG. 20 is an explanatory view showing the principle of a dark field illumination system in the pattern detection system of the invention;

FIG. 21(a) and 21(b) show front and top views, respectively, of parabolic concave mirrors for explaining how to cut the same, used in the system, according to the present invention;

FIG. 22 shows an explanatory view for explaining how to assemble the parabolic concave mirror segments according to the invention;

FIG. 23(a) and 23(b) show top and cross-sectional views, respectively of a mirror segment-gap adjusting device for adjusting the gap between the parabolic concave mirrors in accordance with the invention;

FIGS. 24(a) and 24(b) show the top and side vide views, respectively, of shows a detailed example of the dark field illumination system in accordance with the invention;

FIG. 25 is a perspective view of light fibers arranged in two lines;

FIGS. 26 and 27 show explanatory diagrams for explaining problems occurs in said embodiments;

FIGS. 28 and 29 show respective circuit diagrams of the X-direction and Y-direction positional offset detecting devices;

FIG. 30 shows a pattern-direction decision device used in the system of the invention;

FIG. 31 shows a circuit diagram of the pattern-direction decision device of FIG. 30;

FIG. 32(a), 32(b) and 32(c) show top, front and side views, respectively, of a form of a fine/coarse feed mechanism;

FIG. 33 shows a graph for explanation of the operation of the system according to the invention; and FIG. 34 shows a flowchart for explanation of the operation of the system according to the invention.

Referring now to FIG. 5, there is shown an embodiment of a system of inspecting pattern defects in a photomask. An LSI wafer and a mask as specimens are placed on a movable table 33, and lights are illuminated on the back surface of the mask 2 to be inspected from the light source 3 via the reflecting mirrors 4 and 4' and the condensers 5 and 5'. The lights passed through the mask will be magnified through an optical imaging system which includes the objective lenses 6 and 6', a light-path changing mirror 17, field lenses 18 and 18', a rotary discrete multi-face mirror 19 and imaging lenses 20 and 20'. The magnified lights through the imaging system will be then imaged on parallelly-readable array sensors 21 and 21'. The array sensors 21 and 21' will convert the images formed thereon to electric signals according to the light and dark level of the images, and parallelly supply the electric signals to respective binary circuits 22 and 22'. The binary circuits 22, 22' will sample and convert the electric signals to binary picture element signals to store them into two-dimensional memories 23 and 23'. Respective two-dimensional patterns stored in the memories will be compared by a comparator 24 to thereby detect pattern defects on the basis of the pattern unequal amount.

As the rotary multi-face mirror 19 rotates, the images on the array sensors 21 and 21' will move by a predetermined distance in a direction perpendicular to the linear array sensors, and return to the original positions each time the mirror face of the rotary multi-face mirror 19 in the imaging paths is replaced by the next mirror face through rotation of the multi-face mirror 19. The above image movement or displacement on the array sensors will be cycled as the mirror 19 turns. This image movement will cause elements in the array sensors 21 and 21' to produce electric signals corresponding to the light (bright) and dark levels of the images of the mask pattern in the image movement direction. At the same time, if the movable table 33 is arranged so as to move by a distance W corresponding to the row-direction dimension of the array sensors 21 and 21' in a direction perpendicular or inclined by a predetermined angle with respect to the rotary multi-face mirror 19 during one image scanning cycle thereof, then the entire LSI wafer and mask can be detected with the width W and without any gap therebetween, as shown in FIG. 6 or FIG. 7. When the table 33 is fed or moved in a direction at an angle $\theta$ inclined with respect to the axis of the multi-face mirror 19, the scanning zone will be of a rectangle shape. In this connection, the images run on the array sensors at a high rate, and thus it is desirable that the sensors are high in response speed and high in sensitivity.

In order to realize such array sensors 21 and 21' with a high sensitivity and a high response speed, as shown in FIG. 9, optical fibers 25 are arranged in an array form by means of a holder 26 in the imaging surface so that the lights received at the optical fibers will be guided to the light receiving portions of photoelectric multipliers 28 via respective fiber cables 27 where the photoelectrons are multiplied. In this method, electric signals to which the lights are photoelectrically converted at the light receiving portions, can be amplified $10^4$ to $10^6$ times and thus the sensitivity of the system can be remarkably improved and the present invention can be applied even in the case where the illumination light is relatively weak. More specifically, in this case, one end of each of N light fibers $27_1, 27_2, \ldots, 27_n$ are connected to N respective photo-sensors $28_1, 28_2, \ldots, 28_n$. In this way, the free ends of the N light fibers are used as the light receiving portions of the photo-sensors and are arranged in a straight line L into the light fiber row 27.

Reference characters $V_1$ and $V_2$ are outputs of the photo-sensors $28_1$ and $28_2$.

Turning to FIG. 6, there is shown an example of the field of view by the above optical system, wherein the N light receiving portions of the optical fiber row 27 arrayed in the line L are scanned in the Y-direction perpendicular to the line L so as to parallelly and simultaneously provide N scanning operations ($A_1, A_2, \ldots, A_n$). In FIG. 6, W denotes a scanning width, l denotes a scanning distance and a numeral 30 denotes a scanning range.

The range of the scanning distance l is determined in the following manner. As shown in FIG. 5 the laser spot generated by a laser oscillator 201 is reflected by the mirror 202 and is then directed to the mirror surface of the rotary multi-face mirror 19. A reflected light from the mirror 19 is detected by the light receiver 204 through a slit 203 and is converted by a binary circuit 205 into a binary signal. The binary signal is used as a start signal for starting the scanning operation. The start signal is also used to operate a timer 206. The timer 206 produces an operating signal of a given time duration $l_t$ to thereby provide a scanning end signal. The scanning start signal and the scanning end signal are applied to the comparator 24 to effect a defect detecting operation until application of the end signal after the start signal.

Simultaneously with the above Y-direction scanning operation of the optical fiber row, the pattern under inspection will be fed in the X-direction.

The X-direction feed speed V is set to be W/T where W is the above scanning width, and T is the cycle time necessary to scan by the scanning distance l and also corresponding to the time necessary for the rotary multi-face mirror of regular M-gon section to rotate 1/M turns.

In the case where the free ends of the N light fibers connected at the other ends to the respective N photo-sensors are arranged in the line L and used as light receiving portions as in this embodiment, the light receiving portions (that is, the free ends of the N optical fibers) can be arranged close to each other regardless of the contour dimensions of the photosensors, and thus the scanning density can be easily increased. Further, in the case where the projection light flux of the pattern images is scanned through reflection of the rotary multi-face mirror as in this embodiment, an accurate and high-speed scanning operation can be easily obtained. In addition, since the scanning cycle time depends on a mechanical factor such as the rotational speed of the rotary multi-face mirror, the scanning operation can be easily synchronized with the X-direction feed operation of the patterns.

In FIG. 10, patterns of identical configuration are arranged in an array form in the photomask 2 with its pitch of P. In the case where two patterns 32 and 32' of the mask of FIG. 10 in a distance "d" spaced relation are electrically detected by a pattern detection system (which will be explained later) of FIG. 11, the two detected electric output signals are compared to judge that, if the two output signals are not equal to each other, there exists a defect in the patterns.

FIG. 11 shows the pattern detection system of another embodiment of the present invention in which two sets of detectors are disposed in a distance "d" spaced and parallel relation to each other. More specifically, the two optical fiber rows 27 and 27' and the two objective lenses 6 and 6' are provided and the width dimension D of the rotary multi-face mirror 19 is designed to be greater than the distance "d". Reference numeral 33 is an X-Y stage or table for feeding the photomask 2 to be inspected in the X direction and simultaneously for feeding stepwise the same in the Y-direction, and numeral 17 is the plane mirror 17 for defecting by 90° the optical axis of the projection light flux in order to make the entire system compact.

In this embodiment of FIG. 11, the light receiving portions of the optical fiber rows 27 and 27' connected at the other ends to the respective photosensors are arranged in the line L opposed to the two patterns 32 and 32', the rotary multi-face mirror 19 is provided, for scanning the images of the patterns 32 and 32' in a direction perpendicular to the line L, the X-Y table 33 is provided for feeding the patterns 32 and 32' in a direction parallel to the line L, the arithmetic circuit (comparator) 24 is provided for comparing electrically the outputs of the photosensors ($28_1$ to $28_n$ and $28'_1$ to $28'_n$) connected to said two sets of optical fiber rows 27 and 27', so that the two patterns 32 and 32' will be detected as electric signals simultaneously and parallelly and the two output signals are compared to detect the difference therebetween, whereby the presence or absence of the pattern defects can be automatically detected according to the presence or absence of any detected difference. The system of this embodiment, however, involves the following technical difficulties. That is, the width dimension D of the rotary multi-face mirror 19 must be the length "d" (the distance between the patterns 32 and 32') than the distance between light fluxes on the reflecting face of the rotary mirror 19, as has been explained above. On the other hand, for a high-speed scanning operation, the rotary mirror 19 must be rotated at a high speed over 10,000 to 20,000 r.p.m. As a result, as the width dimension D is made greater, the motor must have a larger power capacity to drive the rotary mirror.

FIG. 12 shows a schematic perspective view of a further embodiment of the pattern detection system according to the present invention wherein the width dimension D of the rotary multi-face mirror 19 can be made smaller to eliminate the above difficulties. The arrangement of the system shown in FIG. 12 will next be explained in comparison with FIG. 11. As in the embodiment of FIG. 11, the two objective lenses 6 and 6' and the two sets of optical fiber rows 27 and 27' are provided so as to be opposed to the two patterns 32 and 32'.

The projection light fluxes of the two patterns which pass through the two objective lenses 6 and 6' are reflected on respective plane mirrors 34 and 34' to meet at a focusing lens 35 arranged in the light paths. The field lenses 18 and 18' disposed in a focusing surface of the objective lenses 6 and 6' have each such a shape (see FIG. 12) as cut off at their insides to cause the two projection light fluxes to come nearer to each other.

In this way, the two objective lenses 6 and 6' are opposed to the two patterns 32 and 32' so that the projection light fluxes which pass through the respective objective lenses will meet at the focusing lens 35 via the respective mirrors 34 and 34'. With such an arrangement, the distance "$d_1$" between the both light fluxes on a reflecting face of the rotary multi-face mirror 19 can be made much smaller than the distance "d" between the two patterns 32 and 32'. As a result, the width dimension D of the rotary mirror 19 can be designed to be smaller and correspondingly the mirror 19 can be easily rotated at a high speed.

Explanation will next be made in more detail with reference to FIG. 11 and FIGS. 13 to 18. The specimen 2 (LSI wafer and mask) has at its surface fine Al wiring patterns and fine circuit patterns. Two points 41a and 41b on the specimen 2 indicate inspection or detection points. Reference numerals 38 and 38' are light sources, numerals 37 and 37' are condensers, and references 36 and 36' are half mirrors. Two incident lights A and B emitted from the light sources 38 and 38' will be illuminated (light field illumination) on the specimen 2 (the inspection points 41a and 41b) via the half mirrors 36 and 36' and the objective lenses 6 and 6'. A comparator 39₁ receives outputs from photosensors 28₁ and 28₁' corresponding to the points 41a and 41b to be inspected for comparison. Similarly, a comparator 39₂ compares outputs from photosensors 28₂ and 28₂' . . . , and a comparator 39ₙ compares outputs from photosensors 28ₙ and 28ₙ'. An OR gate 40 receives at its input terminals the outputs from all the comparators 39₁, 39₂, . . . , 39ₙ.

The specimen 2 is placed on the X-Y table, and the entire surface of the specimen is inspected by means of image scanning operation of the rotary multi-face mirror 19 and specimen scanning operation of the X-Y table. More specifically, in the X-Y table scanning operation, the X-Y table is moved continuously in a direction perpendicular to the image scanning operation of the rotary mirror 19 and moved stepwise in a direction parallel thereto. The amount of the step movement corresponds to the image scanning width of the rotary mirror 19.

With the above arrangement, the points 41a and 41b are moved in synchronism with each other to search for or locate defects in patterns on the specimen. That is, a scanning operation is made on the surface of the specimen 2 so that patterns for every two points to be inspected are compared and detected by the above detection system. The photosensors $39_1, 39_2, \ldots, 39_n$ are the same in structure. There is shown in FIG. 13 a circuit diagram of a form of the comparator $39_n$ which comprises a subtraction circuit 42, an absolute-value generating circuit 43, an analog comparator 44 and a potentiometer 44a for setting a permissible offset ε. The subtraction circuit 42 includes resistors 42a, 42b, 42d, 42e and a differential amplifier 42c. The absolute value circuit 43 includes resistors 43a, 43b, 43c, diodes 43e, 43f and differential amplifiers 43d, 43g. The analog comparator 44 receives an absolute value difference or offset $|V_n|$ from the absolute-valve generating circuit 43 and compares that valve with the permissible offset ε. If $|V_n| > \epsilon$, then the comparator 44 will generate a defect signal.

In the operation of the circuit shown in FIG. 13, the subtraction circuit 42 receives and compares outputs $V_n$ and $V_n'$ from the photosensors $28_n$ and $28_n'$ to generate a difference signal therebetween. The next-stage absolute value circuit 43 receives the difference signal and finds the absolute value $|V_n|$ of the difference signal. The analog comparator 44 compares the absolute value $|V_n|$ with the permissible offset ε. If $|V_n| \leq \epsilon$, then the comparator 44 determines that patterns at the two points 41a and 41b are equal. When $|V_n| > \epsilon$, the comparator 44 determines that the patterns at the two points are not identical and generates a defect signal. The output $|V_n|$ of the absolute-value generating circuit 43 is also used for other processing. As the permissible offset ε is smaller, it becomes difficult to detect finer or minuter defects in the patterns.

The LSI wafer and mask have various types and the chip size is different depending on the type. Therefore, in order to inspect or check different-size chips with the identical system, it is necessary to adjust the gap between the objective lenses 6 and 6' for detection of the identical pattern portions.

In this connection, the gap between the objective lenses is adjusted accurately, but the optical parts and the light receiving portions of optical fibers arranged in light paths from the objective lenses and the optical fibers must be correspondingly adjusted because a movement of the objective lenses causes a movement of the light paths. By accurately adjusting the gap between the objective lenses and by accurately positioning the optical parts and the optical fiber receiving portion, the relative error (offset) between two pattern positions can be minimized and the defect decision accuracy can be improved, allowing inspection or detection of finer pattern defects. In other words, any positional offset signal in detection patterns entered into the two optical fibers must be eliminated for accurate defect decision.

Chips on the specimen might be sometimes placed as offset. Even if patterns for the chips are equal, normal or good patterns will be wrongly judged to be defective so long as the chips are not arranged accurately in X and Y array form. For this reason, the optical system must be re-adjusted for every different set of chips, but this will make it impossible to continuously and automatically check the chip patterns. For a continuous and automatic inspection, it is necessary to always adjust the detecting pattern positions so as not to eliminate the offset between the two detection patterns, while performing the defect decision.

Since the offset amount between chips is usually very small, it is unnecessary to re-adjust the relative position between the objective lenses and optical parts and it is required only to readjust or reposition the light receiving portions of the optical fibers. Therefore, it is important to re-adjust the position of optical fiber receiving portions more accurately for detection decision.

Alternatively, it may be possible to fix one light path (for example, the light path on the right side in FIG. 11), set movable the other light path (for example, the light path on the left side in FIG. 11), and then readjust the position of the detection patterns by moving the other path so as to eliminate the offset amount between the two detection patterns. In this embodiment of FIG. 11, the right side light path has been fixed and the left side light path has been movable, but the reverse arrangement may be employed.

In the case where a different sort of specimen is inspected, the X-Y table (not shown) mounted with the objective lenses 6 and the lenses 18 is positioned in advance before inspection. Under this condition, an accurate defect decision can be carried out only by fine adjusting the light receiving portions of the optical fibers 27 during the inspection operation.

According to the invention, the light receiving portions of the light fibers 27 are mounted on the X-Y table and a positional alignment control device is provided. The positional-alignment control device functions, while judging defects, to receive an output from the pattern inspecting comparator, calculate the positional offset amount, and drive the X-Y table 45 according to the calculated amount to thereby eliminate the positional offset.

Referring now to FIG. 14, there is shown a drive circuit for driving pulse motors 47 and 48 to move the X-Y table 45 in the X and Y directions. A position command circuit 51 generates a command signal indicative of the X- and Y-direction movement amounts and sends it to drivers 49 and 50. The drivers 49 and 50 drive the respective pulse motors 47 and 48 according to the received command signal value. The pulse motors actuate the respective feed screws to move the light receiving portions 25 of the optical fibers up to a desired position. The position command circuit 51 functions to receive at its one input terminal an externally manually entered position command, receive at its other input terminal the error amount with respect to the detected position value during a table movement (that is, feedback control function), calculate the respective X- and Y-displacement amounts according to the position command and error amount entered, and generate the calculated value. The error amount with respect to the detected position value corresponds to the value obtained by inspecting the outputs of the comparators in FIG. 11 upon a positional alignment operation. The details will be given below.

FIG. 15 shows a relation between an array of optical fiber receiving ends 25a and the scanning direction of a real image by the rotary multi-face mirror. In the figure, the fiber end array direction corresponds to the X direction and the direction perpendicular to the X-direction corresponds to the Y direction. Further, the real-image scanning direction by the rotary mirror is shown with an arrow in FIG. 15. Therefore, the Y-direction corresponds to the real-image scanning direction.

FIGS. 16 and 17 show different offset calculation circuits for positional alignment and FIG. 18 is a timing chart of signals appearing therein. The circuit of FIG. 16 is used to calculate an X-direction positional offset and the circuit of FIG. 17 is used to calculate a Y-direction positional offset. Both circuits generate a signal indicative of an error amount with respect to the detected position value.

The positional-offset calculating circuit of FIG. 16 comprises an adder 53, a sample-and-hold circuit 54, and A/D converter 55, an AND gate 56, adder 57, latch circuits 58 and 59, and a comparator 60. The absolute value signals $|V_1|, |V_2|, \ldots, |V_n|$ are applied to the adder 53 from the respective comparators for photosensor outputs, and when compared with FIG. 13, $|V_1|$ corresponds to the absolute value of a difference between $V_1$ and $V_1'$, $|V_2|$ corresponds to the absolute value of a difference between $V_2$ and $V_2'$, ... and $|V_n|$ corresponds to the absolute value of a difference between $V_n$ and $V_n'$. The adder 53 adds $|V_1|, |V_2|, \ldots,$ and $|V_n|$ and finds an X-direction positional offset amount. The sample-and-hold circuit 54 samples and holds the output of the adder 53 and sends the sampled value to the A/D converter 55 where the sampled value is converted from analog to digital. The A/D conversion period and A/D conversion point by the A/D converter 55 are determined by the output of the AND gate 56. The effective range of one input applied to the AND gate 56 is given by a selected time duration in one scanning period of the rotary mirror as shown in FIG. 18 and determined by the view field range of the objective lens. A/D conversion is carried out by a clock pulse during the scanning period. On the other hand, the adder 57 adds all the A/D converted outputs during the effective range of one scanning period and averages the X-direction positional offset amounts within the effective range. The sampling period of the A/D converter 55 depends upon the diameter of the optical fiber receiving faces and the real-image scanning rate by the rotary multi-face mirror. If the diameter of the optical fiber receiving faces is D ($\mu$m) and the real-image scanning rate is "v" (m/sec), then the clock pulse "f" must be v/D (MPPS).

The adder data before one scanning operation of the rotary multi-face mirror and the pulse-motor driving direction are prestored in the latch circuit 59. After the effective range has elapsed, the thus-obtained adder data ($\delta xn$) and an output (adder data $\delta xn-1$ before one scanning operation) from the latch circuit 59 are compared by the comparator. If $\delta xn < \delta xn-1$, the positional offset amount is small and thus the position command circuit 51 drives the pulse motor 47 a selected amount in the same direction as having been driven before one scanning operation. When $\delta xn > \delta xn-1$, the system judges that the positional offset amount became larger and commands the position command circuit 51 to drive the pulse motor 47 a selected amount in the reverse direction or sense. Outputs CW and CCW of the comparator 60 are the comparison results. For example, if $\delta xn > \delta xn-1$, then the signal CW is "1" and when $\delta xn < \delta xn-1$, the signal CCW is "1". Or, the signal CW may be set to have a polarity of ($\delta xn - \delta xn-1$) and the signal CCW may be set to have an offset amount of (δxn−δxn−1), depending on the internal configuration of the position command circuit 51. The signals CW and CCW correspond to the error amounts with respect to the detected position values as explained earlier.

When the pulse motor 47 finishes its turning operation, a newly found adder data is stored in the latch circuit 59, whereby the real-image detection position is adjusted for every one scanning operation so that if an offset occurs the pulse motor 47 will be driven to eliminate the offset. In FIG. 18, the timing signal for driving the pulse motor 47 and the latch pulse applied to the latch circuit 59 are illustrated.

On the other hand, the offset calculation circuit of FIG. 17 comprises a sample-and-hold circuit 61, an A/D converter 62, an AND gate 63, an adder 64, latch circuits 65 and 66, and a comparator 67. The timing of signals appearing in the circuit of FIG. 17 is substantially the same as in FIG. 18. The absolute value (for example, $|V_1|$) of a difference between the associated 20 arbitrary two photo-sensor outputs is selected and supplied into the sample-and-hold circuit 61 which in turn samples and holds the signal $|V_1|$ and sends it to the A/D converter 62. The A/D converter 62 converts the signal from the sample-and-hold circuit 61 to a digital signal under control of the AND gate 63 and sends the digital signal to the adder 64. The adder 64 adds the digital signal to an output (that is, feedback signal) of the latch circuit 65 to latch in the latch circuit 65. The latch output of the latch circuit 65 is compared by the comparator 67 with the previous latch output which has been latched in the latch circuit 66 at the time of the previous scanning operation to compare δyn and δyn−1 at the time of the previous and current scanning operations. The comparison results CW and CCW are supplied from the comparator 67 to the position command circuit 51 to drive the pulse motor 48. The outputs of the comparator 67 correspond to the error amounts and the pulse motor 68 is driven in the direction based on the polarity of the error amount outputs, causing the Y-direction positional alignment operation. Although the photosensors have been used to convert light signals to electric signals in these embodiments, such photoelectric elements as photodiodes may be employed.

According to the above embodiments, automatic inspection can be efficiently effected on LSI wafer or mask patterns. Further, since the real-image detection position is changed so as to eliminate the positional offset amount, finer defects in patterns can be detected, which has been impossible so far in the prior art.

In this way, the optical fibers in the system of the present invention can be easily moved with an accuracy of 1 μm and thus the optical fibers can be readjusted by moving the optical fibers leftward or rightward so as to detect the associated two detection points 41a and 41b in the chip.

A recent increasing tendency is to fabricate high packing density and small size of chips. The inventors of the present invention have thought that the accurate alignment technique between two detection points will form an essential part of the comparative inspective system to meet such demand and have studied the more accurate alignment technique. As a result, the inventors have found the following problems which will be detailed.

Firstly, light receiving portion 100 of the optical fibers is denoted by a numeral 100 in FIG. 26 in which case, the light receiving portion is shown to have 6 elements (numbered 1 to 6 from the left). When a real image 101 of the pattern on the specimen is imaged or focused on the light receiving portion 100, it is assumed that the photosensor produces an output 102 (Vi). On the other hand, when a real image 104 is formed as offset slightly on the light receiving portion 103 on the right side, it is assumed that the photosensor produces an output 105 (Vi').

In this case, the offset adjustment is effected by finding $|Vi-Vi'|$ and by moving the optical fibers 27 in the X direction so that $$\sum_{i=1}^{6} |Vi - Vi'|$$

becomes zero.

A positional offset signal $D_x$ is defined as follows.

$$D_x = \sum_{i=1}^{6} |Vi - Vi'|$$

For an automatic inspection operation, the specimens are fed continuously and thus patterns on the specimens vary with time. Now assume that such a pattern as shown in FIG. 27 has been detected immediately after the pattern of FIG. 26.

As in the case of FIG. 26, consider a numeral 109 be the real image of the left side pattern and a numeral 110 be the real image of the right side pattern. Under this condition, the signal $D_x$ becomes a total of signals 111, 112 and 113. The pattern offset amount in FIG. 27 is the same as that in FIG. 26 but the positional offset signal in FIG. 27 is different from that in FIG. 26. According to inventors' studies, it has been found impossible to align the patterns correctly with each other even if the fiber positions are modified with use of the signal $D_x$.

Secondly, the optical fibers 27 shown in FIG. 11 are moved in the X or Y direction in order to compensate for positional misalignment between the detection points, but it has been found that because the fibers 27 must be moved at a very high speed or rate the use of only the mechanical coarse driving method by means of a combination of pulse motors and ball screws will inevitably cause considerable vibration and further the ball screws are soon worn out.

Explanation will next be directed to an embodiment of the present invention which has resolved the above problems. FIG. 28 shows a circuit diagram of an X-direction positional offset detection device which converts an X direction positional offset to a quantitative signal. In the Figure, the outputs $V_1$ and $V_1'$ of photosensors associated with the left and right light receiving portions 100 and 103 of the optical fibers are supplied to a comparator 120 to generate a difference signal 126. The difference signal 126 is further applied to an element 127 where the absolute value of the difference signal is found. The output signal 128 ($|V_1-V_1'|$) of the element 127 is compared at a comparator 121 with a fixed value $V_c$ so that if $|V_1-V_1'| \geq V_c$ the comparator 121 has a level of "1" and when $|V_1-V_1'| < V_c$ the comparator has a signal of level "0".

When outputs of a group of comparators 129 including the comparator 121 are counted by a counter 123, the counter 123 generates an output pulse signal 140 having N "1" spikes.

On the other hand, the absolute value signal 128 (=$|V_1-V_1'|$) is also applied to a switching transistor 122 to switch it under control of the output of the comparator 121 so that when $|V_1-V_1'| \geq V_C$ the signal $|V_1-V_1'|$ is fed to a sample-and-hold circuit 124. Other outputs of the elements 127 are similarly switched under control of associated outputs of the comparator group 129 and sent to the associated sample-and-hold circuits 124 to sum all the outputs of the switching transistors 121. An output (b) of the sample and-hold circuit 124 and an output (N) of the counter 123 are supplied to a divider 125. An output signal 141 of the divider 125 is expressed by the following equation.

$$\text{signal } 141 = \frac{\sum_{i=1}^{N} |V_i - V_i'|}{N}$$

Where, $|V_i-V_i'|$ is equal to or greater than $V_c$.

Therefore, the output signal 141 will not be affected by the configuration and number of patterns under detection and will be determined only by the positional offset amount of real images in the X direction.

There is shown a Y-direction positional offset detection device which converts a Y direction positional offset to a quantitative signal in FIG. 29. In this embodiment, output signals 132 and 133 of left and right side photosensors are fed to respective A/D converters 134 and 135 and then to respective shift registers 136 and 137. The contents of the shift registers 136 and 137 correspond to those when the patterns on the specimen are detected in the Y direction. Accordingly with use of the register contents, the Y-direction positional offset amount can be converted to a quantitative signal in exactly the same manner as the X-direction positional offset amount shown in FIG. 28.

Turning now to FIG. 30, there is shown a pattern-direction detection device which detects the direction of patterns in order to find the positional offset amount. In the same figure, a group of light receiving portions 139 are scanned by the rotary multi-face mirror 19 shown in FIG. 11 apparently in the Y-direction. Therefore, by storing the signals of the photosensor group only into the zone 140 and examining the information therein, the direction of the real-image patterns can be known.

When a Y-direction pattern 141 is detected, the information in the memory is all the same with respect to the Y-direction. If an X-direction pattern 142 is detected, then the information in the memory is all the same with respect to the X-direction, as the information in the zone 143.

FIG. 31 is a circuit diagram of an example of the pattern direction detection device in which the light receiving portions are "m" in number and numbered 1, 2, 3, . . . , and m from the left. An output signal 145 of a photosensor associated with a light receiving portion 144 is compared by a comparator 146 with a fixed voltage +$V_c$ to convert to a binary signal. The binary signal is loaded into a shift register 147 to allow a circuit 148 to search for the X-direction pattern and a circuit 149 to search for the Y-direction pattern. For example, only when a shift register address (1, 1) contains therein a signal $B_{11}$, an address (1, 2) contains a signal $B_{12}$, . . . , and an address (1, m) contains a signal $B_{1m}$ and at the same time when $B_{11}=B_{21}=B_{31}$, $B_{12}=B_{22}=B_{23}$, . . . , $B_{1m}=B_{2m}=B_{3m}$, then a NAND element 150 has at its output terminal a level "1". Therefore, when the output of the NAND element 150 is "1", it is judged that the X direction pattern is under detection. Similarly, when $B_{11}=B_{12}=B_{13}$, $B_{21}=B_{22}=B_{23}$, . . . , and $B_{m1}=B_{m2}=B_{m3}$ are satisfied, a NAND element 151 has its output terminal a level "1" and it is judged that the Y-direction pattern is under detection.

Next, a fine/coarse feed mechanism for finely and coarsely feeding or moving the tip ends of the optical fibers in the X and Y directions are shown in FIG. 32. The fine/coarse feed mechanism includes a fine feed device 153 for finely moving a tip end 152 of a optical fiber and a coarse feed device 158 for coarsely moving the entire fine feed device 153. In this embodiment, piezo elements are used as fine-feed power source. The piezo element is high in response speed, small in size and light in weight. When supplied with a voltage, the element elongates a very small amount of 10 to 20 μm in its longitudinal direction. The tip end 152 of the optical fiber is supported by two fine feed piezoelectric elements and two plate springs so that, for example, when an X-fine feed piezo element 154 is elongated a very small amount in the X-direction, the optical fiber tip end 152 will pivot a very small amount in the X-direction on an X-direction fine feed piezoelectric element 155 as a pivot point. Likewise, when a Y-fine feed piezoelectric element 156 is elongated a very small amount in the Y-direction, the optical fiber tip end 152 will pivot a very small amount in the Y-direction on a Y-fine feed plate spring 157 as a pivot point.

In this way, the optical fiber tip end 152 can be moved predetermined distances in the X- and Y-directions at a high speed.

In order to move a relatively large distance the entire fine feed device 153, the coarse feed device 158 is provided. That is, the entire fine feed device 153 is coarsely moved in the X-direction by a pulse motor 159 and in the Y-direction by a pulse motor 160.

The operation of the embodiment with the above-mentioned arrangement will next be explained. Fine adjustment for the detection points 41a and 41b of the left and right patterns is carried out by relatively moving the optical fibers 27 and 27' in the X- and Y-directions.

Explanation will be made as to the case where the optical fiber 27 is moved in the X-direction. Consider that a displacement amount of the optical fiber is $\epsilon$, then a difference 131 between the outputs of the right and left photosensors in the device (see FIG. 8) used for determining an actual X-direction displacement difference is expressed by a function $f(\epsilon)$ which corresponds to an X-direction positional displacement amount.

Suppose that if $\epsilon=0$, $f(\epsilon)=0$, so that the relation between $\epsilon$ and $f(\epsilon)$ is as shown in FIG. 33 wherein "u" is a displacement 161 by the fine feed device and "w" is a displacement 162 by the coarse feed device.

In general, three different voltages 0, 200 and 400 V are applied to the piezoelectric element and thus the optical fiber is moved or displaced at points $\epsilon_1$, $\epsilon_2$ and $\epsilon_3$ in FIG. 33. Let $w_c$ be an unit displacement by the pulse motor and $f_c$ be a fixed voltage value. If $f(\epsilon_3)-f(\epsilon_1) \geq f_c$, then the pulse motor is driven to provide a displacement $-w_c$. When $|f(\epsilon_3)-f(\epsilon_1)| < f_c$, the pulse motor is stopped. If $f(\epsilon_3)-f(\epsilon_1) \leq f_c$, then the pulse motor is driven to provide a displacement $+w_c$.

In this way, coarse adjustment is effected by driving the motor in such a direction that the X-direction positional displacement is made smaller.

The operation of the entire system will be explained in connection with a flowchart of FIG. 34. Initially, the piezoelectric element is positioned at the point $\epsilon_1$ and the system is kept waiting until the NAND element 150 produces a signal "1". When the signal has a level of "1", this means that the X-direction pattern is under detection. Thus, the system stores $f(\epsilon_1)$, calculates $f(\epsilon) - f(\epsilon_1)$ and determines a desired amount that the motor is to turn. Next, the system displaces the piezoelectric element at the point $\epsilon_3$ and waits until the NAND element again produces a signal "1". As soon as the signal has a level of "1", the system will store $f(\epsilon_3)$. In this way, the X-direction positional alignment operation is effected. The same explanation is applied to the Y-direction positional alignment operation.

As has been explained in the foregoing, actual displacement differences between two detection points in the X- and Y-directions are determined by means for converting to a quantitative signal the relation between the images detected by two image detection elements, and the optical fibers are moved by fine/coarse displacement means so as to make smaller said X- and Y-direction displacement differences with use of means for detecting the pattern direction, whereby the two detection points are aligned with each other. As a result, according to the present invention, there can be provided a pattern comparison check system which will not be affected by the configuration and number of patterns under detection, which allows an accurate pattern alignment at a high speed, which allows a positional alignment between left and right patterns at all time even while patterns on the specimen are being detected, and which allows a complete automation for the purpose of high quality products and mass production.

On the other hand, an A1 wiring pattern 68, for example is formed on recessed and projected (or stepped) portions of a wafer. Therefore, in order for lights reflected by the pattern to arrive at the objective lenses 6 and 6', it is indispensable to combine the light field illumination and the dark field illumination. FIG. 19 shows a combined light and dark field illumination where a light field illumination light 60 and a dark field illumination light 61 are directed to a point 69 on the wafer. For the above-mentioned comparative check, it is necessary to direct lights to the points 41a and 41b by the combined light/dark field illumination method, as shown in FIG. 11. The light field illumination can be realized, as shown in FIG. 11, by illuminating the points upward from the lamps 38 and 38' via the condensers 37 and 37', but the dark field illumination requires proper arrangement (which will be explained later).

The principle of the present invention is shown in FIG. 20 wherein two parabolic concave mirrors 70 and 71 are arranged above the wafer so that light is directed to the point 41a via the mirror 70 and light is directed to the point 41b via the mirror 71. The mirrors 70 and 71 are cut along their radial directions and assembled together in order to allow a simultaneous provision thereof.

The distance between the two detection points 41a and 41b must be changed according to the application purpose. In FIG. 20, the objective lens 6 is set to be movable while the objective lens 6' is set to be stationary or fixed, a reference distance between the points is set to be W, and the lens 6 is set to be able to move ±S/2 relative to the reference position and correspondingly the parabolic concave mirror 70 can move ±S/2 relative to the reference position.

First, explanation will be directed to how to cut a parabolic concave mirror along its radial direction. In FIG. 21, a ring-shaped parabolic concave mirror 74 with its center 75 is circumferentially equally cut by radial lines which each pass a center 76 a distance W/2 spaced from the point 75 and have a width S/2, as illustrated. In this embodiment of FIG. 21, the circumference of the mirror 74 is equally divided into 48 segments.

Next, after the concave mirror segments divided as shown in FIG. 21 are circumferentially alternately removed as shown with zones with inclined lines and after 180° rotation on the center 76, again placed in the original position; the mirror segments are disposed as shown in FIG. 22. For convenience of the explanation, mirror zones or segments with inclined lines are called the zones B and mirror segments without inclined lines are called the zones A. The zones A have the center 75 and the zones B have a center 77, with a distance W between the centers 75 and 77. Since there is a ±S/2 between the zones A and B and the zone B can be moved ±S/2 in an arrow (78 in FIG. 22) direction, the dark field illumination points on the wafer can be changed.

Explanation will be made as to an embodiment wherein the zones A and B of the parabolic concave mirror are mounted independently and the zones B are moved in the arrow (78 in the figure) direction. In FIG. 23, the zones A in the parabolic concave mirror are fixedly mounted on a lower base 80 by a supporter 79 and the zones B therein are fixedly mounted on an upper base 82 by a supporter 81. The upper base 82 in turn is connected to a side base 83 via a roller guide so as to move freely in arrow (86 in FIG. 23) directions by means of a motor 84 and a screw 85. In this way, the distance W in FIG. 20 can be freely changed.

Referring to FIG. 24, there is shown an embodiment of the pattern detection system according to the present invention. Lights emitted from a mercury-arc lamp or a halogen lamp 91 (disposed at a focus point of a parabolic concave mirror 92) are reflected upward at the mirror 92 in parallel directions and then are directed again upward parallelly via reflecting mirrors 93 and 94. The same optical system as this system is provided on the left side and similarly lights are directed upward parallelly from the mirror 94. With this pattern detection system, two points on a wafer can be simultaneously illuminated uniformly and intensely from the periphery. In this case, the wafer 2 is fixed on a wafer chuck 90 by the chuck portion thereof and the chuck 90 is fixedly mounted on the X-Y table 33. As the X-Y table moves in the X- and Y-directions, the wafer 2 will correspondingly move in the X- and Y-directions, whereby the entire surface of the wafer is checked through the objective lenses 6 and 6'.

The Y-direction scanning operation and the X-direction scanning operation are effected at the same time as has been explained in the foregoing, the scaning direction will be oblique to the pattern surface, as shown in FIG. 7, a rectangular scanning zone 30 in FIG. 6 corresponds to a parallelogrammic scanning zone 30' in FIG. 7 and the scanning zone 30' moves continuously in the X-direction to form a strip-shaped zone 31 of a width l. An arrow B denotes the pattern feeding direction. After the strip zone 31 on the pattern has been scanned, a step feed operation is effected a distance 1 in the Y-direction (the same as an arrow C-direction in FIG. 8) and at the same time, the pattern feeding direction is reversed in such a direction as shown by an arrow B'. The above operation is repeated to scan the entire surface of the pattern, so that N time-series output signals parallelly obtained are compared and calculated, whereby the pattern defects can be detected.

It will be easily understood from the above explanation that, the time necessary to scan can be reduced 1/N times when compared with that in the prior art under the same scanning rate and the same scanning density, because N scanning operations in the directions of the arrows $A_1$, $A_2$, ... and $A_N$ in FIG. 6 can be parallelly effected in accordance with the invention although these scanning operations are sequentially continuously with respect to time in the prior art.

In this way, the embodiments disclosed above have an advantage that two detection points on a wafer can be easily dark-field illuminated by a simple optical system. As a result, patterns at two points on a specimen can be imaged to compare signals resulting from the obtained pattern images for inspection of the patterns. For example, it is possible to automatically inspect Al patterns on a recessed and projected face of an LSI wafer. Further, according to the invention, the inspection can be carried out at a rate higher by 10 to 50 times than the conventional visual inspection and the inspection reliability can be remarkably improved.

If a minute or fine defect exists in the boundary or interface between the optical fibers $27_{n-1}$ and $27_n$, the detected output for the defect is diverged into the two optical fibers, which might make it impossible to detect the defect. In addition, it is difficult to arrange the light receiving portions of optical fibers tightly closer to each other so that the portions have each a complete square shape. Such problems can be resolved, as shown in FIG. 25, by arranging the optical fibers in two rows so that the upper and lower light receiving portions thereof are shifted a distance u/2 (where "u" is a width of the each portion) in the row direction.

We claim:

1. A pattern detection system comprising:
   illumination means;
   first means for linearly moving objects to be measured in a first direction so that said objects are illuminated by lights from said illumination means;
   an optical system for imaging the objects to be measured;
   second means including a rotary multi-faced mirror for repeatedly scanning the objects to be measured in a second direction intersected at a predetermined angle with respect to the direction of the objects moved by said first means;
   a plurality of photosensor means each including a photosensor array arranged in a direction perpendicular to the direction of images scanned by said second means, on the surface of which said images are formed through said optical system, and for generating respective outputs in a multiplexed manner;
   wherein said first means includes means for constantly advancing the objects in said first direction at a speed such that the objects will move through a distance corresponding to the optical length of a photosensor array during one scanning period of the rotary mirror while the rotary mirror is scanning so that resulting skew scan of the objects is effected to thereby detect optical images of the objects in said photosensor arrays.

2. A pattern detection system as set forth in claim 1, wherein at least two rows of said plurality of photosensor means are arranged so that the upper and lower photosensors means are shifted in the row direction by a distance corresponding to half of a pitch of the each photosensor.

3. A pattern detection system as set forth in claim 1, wherein said plurality of photosensor means each comprise an optical fiber and a photosensor.

4. A pattern detection system as set forth in claim 1, wherein said first means comprises means for reciprocating the objects along said first direction while indexing the objects in said second direction for each reciprocation in said first direction so that said resulting skew scan of the objects provides a herringbone-like pattern.

5. A pattern detection system comprising:
   illumination means;
   first means for linearly moving objects under measurement in a first direction on which lights from said illumination means are illuminated or through which lights are passed;
   a plurality of optical systems each for imaging respective images of different positions on said objects to be measured;
   second means including a rotary multi-faced mirror, by simultaneously cyclically deflecting lights of said images, for repeatedly scanning the objects in a second direction perpendicular to said first direction with respect to the surface of the objects moved by said first means;
   a plurality of groups of photosensor means provided in association with the pitch of zones arranged above said objects, said plurality of photosensor means being arranged linearly in a direction perpendicular to the direction of said images scanned by said second means, on the surface of which said images are formed through said optical systems, and for generating respective outputs;
   said first means including means for constantly moving the objects in said first direction at a speed such that the objects will move through a distance corresponding to the optical length of a group of photosensor means during one scanning period of the rotary mirror while the rotary mirror is scanning so that a resulting skew scan of the objects is effected to thereby detect optical images as a result of the skew scanning of the objects; and
   comparison means for comparing positionally associated ones of the video signals obtained from said plurality of groups of photosensor means with each other to determine defects in the patterns.

6. A pattern detection system as set forth in claim 5, further including displacement means mounted with one group of said photosensor means for positional adjustment, quantitative means for converting associated picture images detected by said plural groups of photosensor means to quantitative signals to detect offset amounts between the associated picture images, means for detecting the pattern direction in said picture images, and control means for determining said offset amounts between the picture images detected by said quantitative means on the basis of signals obtained from said pattern direction detection means to thereby compensatively actuate said displacement means.

7. A pattern detection system as set forth in claim 6, wherein said quantitative means finds differences between signals associated in two picture images, finds a sum of the number of significant ones of said differences and a sum of analog values to which said significant differences are converted, averages, divides or averages said analog value sum by said summed significant difference number, and decides that the positional offset amount corresponds to said average value.

8. A pattern detection system as set forth in claim 6, wherein said displacement means comprises coarse displacement means and fine displacement means.

9. A pattern detection system as set forth in claim 5, wherein said illumination means comprises a dark field illumination means device having combined parabolic concave mirrors at whose focus points at least two detection points in said objects are positioned for providing a dark field illumination on said two detection points, and light field illumination means for providing a light field illumination on said two detection points.

10. A pattern detection system as set forth in claim 9, wherein said parabolic concave mirrors each comprise radially-cut segments of an annular parabolic concave mirror.

11. A pattern detection system comprising:
illumination means;
means for linearly moving objects under measurement so that lights from said illumination means are illuminated on said objects;
a plurality of optical means each for imaging respective images of different positions on said objects to be measured;
a plurality of photosensor means on the surface of which said images are formed through said optical means, and for generating respective output image signals;
comparison means for comparing positionally associated ones of the image signals obtained from each of photosensor means to determine defects in the patterns;
displacement means mounted with one of said photosensor means for positional adjustment;
quantitative means for converting image signals detected by said photosensor means to quantitative signals representing the positional difference between the image signals to detect offset amounts between the associated images;
pattern direction detection means for detecting the pattern direction in said images; and
control means for determining said offset amounts between the images detected by said quantitative means on the basis of signals obtained from said pattern direction detection means to thereby compensatively actuate said displacement means.

* * * * *